(12) United States Patent
Liu et al.

(10) Patent No.: US 10,319,170 B2
(45) Date of Patent: Jun. 11, 2019

(54) FOLDED BILL IDENTIFICATION METHOD AND DEVICE

(71) Applicant: GRG Banking Equipment Co., Ltd., Guangzhou, Guangdong (CN)

(72) Inventors: Guanglu Liu, Guangdong (CN); Jian Chen, Guangdong (CN); Zhuming Xiao, Guangdong (CN); Weirui Zheng, Guangdong (CN)

(73) Assignee: GRG Banking Equipment Co., Ltd., Guangzhou, Guangdong (CN)

( * ) Notice: Subject to any disclaimer, the term of this patent is extended or adjusted under 35 U.S.C. 154(b) by 9 days.

(21) Appl. No.: 15/544,379

(22) PCT Filed: Jul. 13, 2015

(86) PCT No.: PCT/CN2015/083861
§ 371 (c)(1),
(2) Date: Jul. 18, 2017

(87) PCT Pub. No.: WO2016/123903
PCT Pub. Date: Aug. 11, 2016

(65) Prior Publication Data
US 2018/0268634 A1    Sep. 20, 2018

(30) Foreign Application Priority Data
Feb. 4, 2015    (CN) .......................... 2015 1 0059223

(51) Int. Cl.
*G07D 7/10* (2006.01)
*G07D 7/183* (2016.01)
(Continued)

(52) U.S. Cl.
CPC ......... *G07D 7/183* (2017.05); *G01N 21/3563* (2013.01); *G06K 9/4609* (2013.01);
(Continued)

(58) Field of Classification Search
CPC ........ G07D 7/183; G07D 7/12; G07D 7/2008; G07D 7/2041; G07D 2207/00; G06K 9/6284; G06K 9/4609; G01N 21/3563
See application file for complete search history.

(56) References Cited

U.S. PATENT DOCUMENTS 4,984,280 A * 1/1991 Abe .................. G07D 7/12
382/135
6,040,584 A * 3/2000 Liu .................... G01N 21/88
194/207

(Continued)

FOREIGN PATENT DOCUMENTS

| CA | 2 362 121 A1 | 11/2000 |
|---|---|---|
| CN | 102236897 A | 11/2011 |

(Continued)

OTHER PUBLICATIONS

International Search Report for Application No. PCT/CN2015/083861 dated Sep. 24, 2015.

(Continued)

*Primary Examiner* — Qian Yang
(74) *Attorney, Agent, or Firm* — Wolf, Greenfield & Sacks, P.C.

(57) ABSTRACT

A folded bill recognizing method and a folded bill recognizing device are provided. The folded bill recognizing device includes: a bill input port configured to receive a to-be-recognized bill or a sample bill; a signal collecting module configured to collect a CIS image of the bill, to obtain an infrared transmission image T and an infrared reflection image F; a signal recognizing module configured to recognize whether the to-be-recognized bill has a fold; and a receiving/rejecting module configured to perform a receiving or rejecting operation on the to-be-recognized bill. The device can effectively recognize a folded bill.

9 Claims, 2 Drawing Sheets

(51) Int. Cl.
   *G07D 7/00*       (2016.01)
   *G01N 21/3563*    (2014.01)
   *G06K 9/46*       (2006.01)
   *G06K 9/62*       (2006.01)
   *G07D 7/12*       (2016.01)
   *G07D 7/20*       (2016.01)
   *G07D 7/202*      (2016.01)

(52) U.S. Cl.
   CPC ............ *G06K 9/6284* (2013.01); *G07D 7/00* (2013.01); *G07D 7/12* (2013.01); *G07D 7/20* (2013.01); *G07D 7/2008* (2013.01); *G07D 7/2041* (2013.01); *G07D 2207/00* (2013.01)

(56) References Cited

U.S. PATENT DOCUMENTS

| | | | |
|---|---|---|---|
| 2007/0000822 A1 | 1/2007 | Yoshioka | |
| 2009/0014946 A1* | 1/2009 | Nagura | B65H 31/18 |
| | | | 271/220 |
| 2009/0285470 A1* | 11/2009 | Takai | G07D 7/164 |
| | | | 382/135 |
| 2010/0054551 A1 | 3/2010 | Decoux | |
| 2013/0034290 A1 | 2/2013 | Lee et al. | |
| 2013/0088712 A1 | 4/2013 | Holl et al. | |
| 2015/0003717 A1 | 1/2015 | Lee et al. | |

FOREIGN PATENT DOCUMENTS

| | | |
|---|---|---|
| CN | 102881074 A | 1/2013 |
| CN | 203812312 U | 9/2014 |
| CN | 104573700 A | 4/2015 |
| EA | 008554 B1 | 6/2007 |
| JP | 2010-117803 A | 5/2010 |
| KR | 20130014920 A | 2/2013 |
| RU | 2004130431 A | 1/2006 |
| RU | 2315359 C2 | 1/2008 |
| WO | WO 03/077209 A2 | 9/2003 |
| WO | WO 2010/151305 A2 | 12/2010 |

OTHER PUBLICATIONS

Written Opinion of the International Searching Authority for Application No. PCT/CN2015/083861 dated Sep. 24, 2015.
Extended European Search Report for Application No. EP 15880858.4 dated Feb. 28, 2018.
Russian Office Action for Application No. RU 2017130019/08(052308) dated Apr. 28, 2018.

* cited by examiner

ND DEVICE

This application is the national phase of International Patent Application No. PCT/CN2015/083861, titled "FOLDED BILL IDENTIFICATION METHOD AND DEVICE", filed on Jul. 13, 2015, which claims priority to Chinese Patent Application No. 201510059223.X, titled "FOLDED BILL RECOGNITION METHOD AND DEVICE", filed on Feb. 4, 2015 with the State Intellectual Property Office of the People's Republic of China, both of which are incorporated herein by reference in their entireties.

FIELD

The present application relates to the technical field of financial self-service device, and particularly to a folded bill recognizing device and a folded bill recognizing method.

BACKGROUND

A folded bill, as a kind of non-circulating bill, is not suitable for circulation any more. Therefore, when a folded bill is inputted into a recognition device, the recognition device needs to recognize and classify it as a non-circulating bill.

Limited to factors such as a conventional imaging device, illumination variations, imaging environments, signals obtained by a signal collecting module of a self-service device is not robust enough, which make a characteristic in the signal of a folded bill insignificant, resulting in difficulties in recognizing a folded bill.

Characteristic description is a key premise of the folded bill recognition. Based on a currently used signal, if only a single-characteristic description method, such as a conventional approach of calculating simply a gray mean value or an approach of performing binaryzation on an image with a threshold and counting abnormal pixels, is adopted, it is difficult to distinguish the folded bills from interfered or fouled bills. The main reason that the conventional characteristic description cannot lead to a good effect is that the folded bills and the interfered or fouled bills are not effectively distinguished or pre-processed.

SUMMARY

In order to solve the problem that it is difficult to distinguish the folded bills from the interfered or fouled bills in the conventional technology, a method and a device for recognizing a fold bill are provided according to the present disclosure. By adopting a characteristic classifying method based on high/low pass filters to effectively describe characteristics of a characteristic field of a bill fold, recognizing performance of a recognition device is improved.

The folded bill recognizing device provided according to the present disclosure includes: a bill input port, configured to receive a to-be-recognized bill or a sample bill and convey the bill to a next module; a signal collecting module, configured to collect a CIS image of the bill to obtain an infrared transmission image T and an infrared reflection image F; a signal recognizing module, configured to recognize whether the to-be-recognized bill has a fold; and a receiving/rejecting module, configured to perform a receiving or rejecting operation on a to-be-recognized bill. The signal recognizing module includes: a first high-pass filtering unit, configured to filter the infrared transmission image T to obtain a high-pass infrared transmission filtering image gT; a first low-pass filtering unit, configured to filter the infrared transmission image T to obtain a low-pass infrared transmission filtering image dT; a second high-pass filtering unit, configured to perform high-pass filtering on the infrared reflection image F synchronously to the low-pass filtering performed on the infrared transmission image T according to a geometric coordinate point to point mapping relationship, to obtain a high-pass infrared reflection filtering image gF; a second low-pass filtering unit, configured to perform low-pass filtering on the infrared reflection image F synchronously to the high-pass filtering performed on the infrared transmission image T according to the geometric coordinate point to point mapping relationship, to obtain a low-pass infrared reflection filtering image dF; a differential filtering image unit, configured to perform a differential operation on the high-pass infrared reflection filtering image gF and the low-pass infrared transmission filtering image dT to obtain a differential filtering image cFT; a first characteristic extraction unit, configured to perform characteristic extraction on the high-pass infrared transmission filtering image gT by calculating an average gray value gT_G of the gT as a characteristic value; a second characteristic extraction unit, configured to perform characteristic extraction on the low-pass infrared reflection filtering image dF by calculating an average gray value dF_G of the dF as a characteristic value; a third characteristic extraction unit, configured to perform characteristic extraction on the differential filtering image cFT by calculating an average gray value cFT_G of the cFT as a characteristic value; a recognition decision unit, configured to calculate models for distinguishing folded bills and non-folded bills based on the characteristic value gT_G, the characteristic value dF_G and the characteristic value cFT_G of sample bills and make a decision whether the to-be-recognized bill has a fold based on a bill classifying decision model. The bill classifying decision model is: in a case that $p_1 > T_1$, $p_2 > T_2$, $p_3 > T_3$ are all true, the to-be-recognized bill is recognized as the folded bill; in a case that $p_1 > T_1$, $p_2 > T_2$, $p_3 > T_3$ are not all true, the to-be-recognized bill is recognized as a non-folded bill. $p_1$, $p_2$ and $p_3$ are confidence levels for determining the to-be-recognized bill as a folded bill, $T_1$, $T_2$ and $T_3$ are three confidence level thresholds.

Preferably, the bill classifying decision model may be further amended as:

$$p_s = \alpha * p_1 + \beta * p_2 + \gamma * p_3, \begin{cases} > T_s & \text{folded bill} \\ \leq T_s & \text{non-folded bill} \end{cases};$$

wherein, $p_1$, $p_2$ and $p_3$ are the confidence levels for determining the to-be-recognized bill as a folded bill, $\alpha, \beta, \gamma$ are different weighted values assigned to p1, p2 and p3 respectively, and $\alpha + \beta + \gamma = 1$, $\alpha \geq 0$, $\beta \geq 0$, $\gamma \geq 0$, $T_s$ is a threshold and has an empirical value of 0.5.

A folded bill recognizing method is also provided according to the present disclosure, which includes: step 1, receiving, by a bill input port, a to-be-recognized bill and conveying the to-be-recognized bill to a signal collecting module; step 2, collecting, by the signal collecting module, a CIS image signal of the to-be-recognized bill to obtain an infrared transmission image $T_s$ and an infrared reflection image $F_s$; step 3, filtering, by a first high-pass filtering unit, the infrared transmission image $T_s$ to obtain a high-pass infrared transmission filtering image $gT_s$; step 4, filtering, by a first low-pass filtering unit, the infrared transmission image to obtain a low-pass infrared transmission filtering image $dT_s$; step 5, performing high-pass filtering, by a second high-pass filtering unit, on the infrared reflection image $F_s$ synchronously to the low-pass filtering performed on the infrared transmission image $T_s$ according to a geometric coordinate point to point mapping relationship, to obtain a high-pass infrared reflection filtering image $gF_s$; step 6, performing low-pass filtering, by a second low-pass filtering unit, on the infrared reflection image $F_s$ synchronously to the high-pass filtering performed on the infrared transmission image $T_s$ according to the geometric coordinate point to point mapping relationship, to obtain a low-pass infrared reflection filtering image $dF_s$; step 7, performing, by a differential filtering image unit, a differential operation on the high-pass infrared reflection filtering image $gF_s$ and the low-pass infrared transmission filtering image $dT_s$ to obtain a differential filtering image $cFT_s$; step 8, performing, by a first characteristic extraction unit, characteristic extraction on the high-pass infrared transmission filtering image $gT_s$ by calculating an average gray value $gT\_G_s$ of the $gT_s$ as a characteristic value; step 9, performing, by a second characteristic extraction unit, characteristic extraction on the low-pass infrared reflection filtering image $dF_s$ by calculating an average gray value $dF\_G_s$ of the $dF_s$ as a characteristic value; step 10, performing, by a third characteristic extraction unit, characteristic extraction on the differential filtering image $cFT_s$ by calculating an average gray value $cFT\_G_s$ of the $cFT_s$ as a characteristic value; step 11, substituting the characteristic value $gT\_G_s$, the characteristic value $dF\_G_s$ and the characteristic value $cFT\_G_s$ respectively into three models $y_1, y_2, y_3$ for distinguishing folded bills and non-folded bills, $$y_1 = f_1(gT\_G);$$

$$y_2 = f_2(dF\_G);$$

$$y_3 = f_3(cFT\_G);$$

to obtain $$p_1 = f_1(gT\_G_s);$$

$$p_2 = f_2(dF\_G_s);$$

$$p_3 = f_3(cFT\_G_s);$$

where $p_1$, $p_2$ and $p_3$ are confidence levels for determining the to-be-recognized bill as a folded bill; in a case that $p_1 > T_1$, $p_2 > T_2$, $p_3 > T_3$ are all true, the to-be-recognized bill is recognized as the folded bill; in a case that $p_1 > T_1$, $p_2 > T_2$, $p_3 > T_3$ are not all true, the to-be-recognized bill is recognized as a non-folded bill; $T_1$, $T_2$ and $T_3$ are three confidence level thresholds, and their empirical values are general 0.5.

Preferably, the step 11 further includes: assigning different weighted values $\alpha, \beta, \gamma$ to $p_1$, $p_2$ and $p_3$, where $\alpha + \beta + \gamma = 1$, $\alpha \geq 0$, $\beta \geq 0$, $\gamma \geq 0$, and determining a threshold $T_s$. The bill classifying decision model is as follows:

$$p_s = \alpha * p_1 + \beta * p_2 + \gamma * p_3, \begin{cases} > T_s & \text{fold bill} \\ \leq T_s & \text{non-foled bill} \end{cases}$$

Preferably, a method for obtaining the three models $y_1, y_2, y_3$ for distinguishing folded bills and non-folded bills includes: collecting a certain number of samples of folded bills and non-folded bills; obtaining, for each of the samples, a characteristic value of an average gray value $gT\_G$ of a high-pass infrared transmission filtering image $gT$, a characteristic value of an average gray value $dF\_G$ of a low-pass infrared reflection filtering image $dF$ and a characteristic value of an average gray value $cFT\_G$ of a differential filtering image $cFT$; counting the characteristic value of the $gT\_G$, the characteristic value of the $dF\_G$ and the characteristic value of the $cFT\_G$ respectively, to obtain a probability distribution graph of the $gT\_G$, a probability distribution graph of the $dF\_G$ and a probability distribution graph of the $cFT\_G$ corresponding to the folded bill as the following formulas:

$$y_1 = f_1(gT\_G);$$

$$y_2 = f_2(dF\_G);$$

$$y_3 = f_3(cFT\_G);$$

where $y_1, y_2, y_3$ are the three models for distinguishing folded bills and non-folded bills respectively.

Particularly, a method for obtaining, for each of the samples, the characteristic value of the average gray value $gT\_G$ of the high-pass infrared transmission filtering image $gT$, the characteristic value of the average gray value $dF\_G$ of the low-pass infrared reflection filtering image $dF$ and the characteristic value of the average gray value $cFT\_G$ of the differential filtering image $cFT$ is the same as the method for obtaining the characteristic value of the average gray value $gT\_G_s$ of the high-pass infrared transmission filtering image $gT_s$, the characteristic value of the average gray value $dF\_G_s$ of the low-pass infrared reflection filtering image $dF_s$ and the characteristic value of the average gray value $cFT\_G_s$ of the differential filtering image $cFT_s$ of the to-be-recognized bill.

Preferably, step 1 to step 10 are not executed in the listed sequence. Step 3 and step 4 may be executed at the same time. Step 5 and step 6 may be executed at the same time. Step 8 may be executed right after step 3. Step 9 may be executed right after step 6, and step 10 may be executed right after step 7.

Specifically, for the image signals $T_s$ and $F_s$, a high-pass filter threshold and a low-pass filter threshold are calculated before step 3: firstly, calculating an average gray value of $T_s$:

$$avG = \sum_{i=1}^{w*h} pix(i)/(w*h);$$

where $pix(i)$ is a gray value corresponding to a pixel of $T_s$, w is the width of the $T_s$ image signal, h is the height of the $T_s$ image signal; and calculating the high-pass filter threshold corresponding to $T_s$ as $T_{11} = j * avG$, $1 \leq j \leq (255/avG)$, the low-pass filter threshold corresponding to $T_s$ as $T_{22} = k * avG$, $0 \leq k \leq 1$.

Specifically, a calculating model for calculating the average gray value $gT\_G_s$ of the $gT_s$, a calculating model for calculating the average gray value $dF\_G_s$ of the $dF_s$ and a calculating model for calculating the average gray value $cFT\_G_s$ of the $cFT_s$ are the same as the calculating models for calculating the average gray values of the $T_s$.

The advantages of the disclosure are as follows.

As the method of high/low pass filters is adopted to effectively classify characteristics, a distinguishability of the characteristics is highly improved. Particularly, different characteristics correspond to different classifiers. Among the classifiers, they have functions similar to the Adaboost classifier, which may ensure a recognition confidence level of the recognizing device of the disclosure and make the recognition system more robustly compatible with complex situations such as an environmental interference, a fouled bill. The folded bill recognizing method and device may effectively recognize a folded bill.

DETAILED DESCRIPTION OF EMBODIMENTS

In order to further illustrate the method and folded bill recognizing device provided in the disclosure, an embodiment is described specifically in conjunction with figures.

Figure 1:
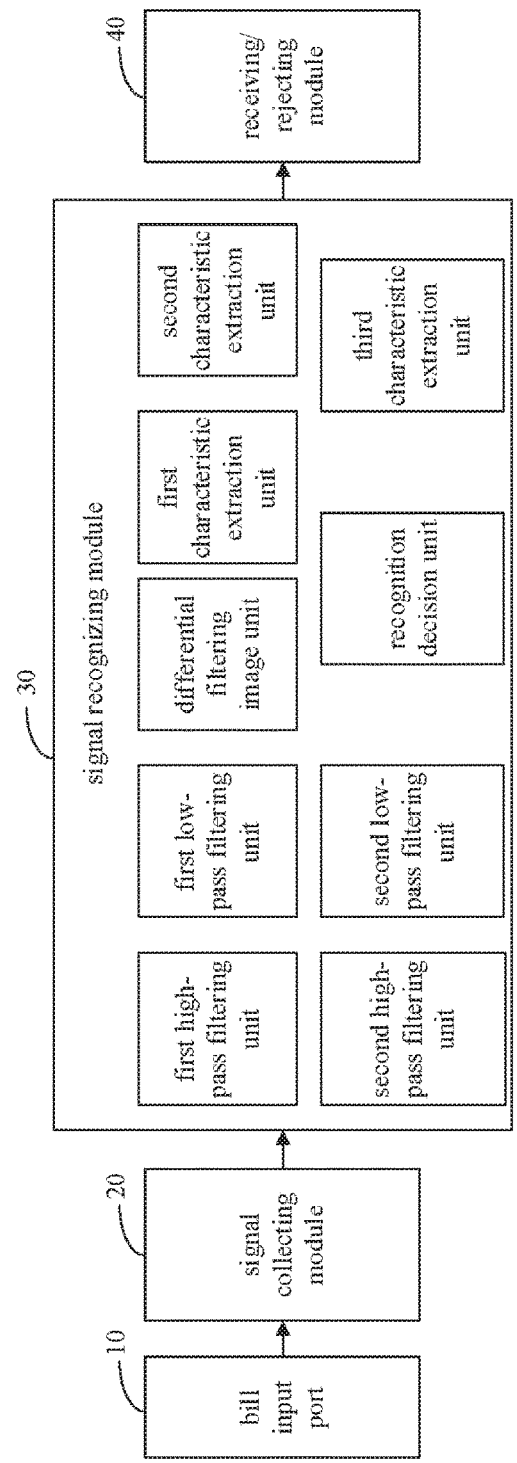
FIG. 1 is a schematic structural diagram of a folded bill recognizing device according to a preferred embodiment of the disclosure.

A folded bill recognizing device is provided according to an embodiment. As shown in FIG. 1, the folded bill recognizing device include a bill input port 10, a signal collecting module 20, a signal recognizing module 30 and a receiving/rejecting module 40.

The bill input port 10 is configured to receive a to-be-recognized bill or a sample bill and convey the bill to a next module. The signal collecting module 20 is configured to collect a CIS image of the bill to obtain an infrared transmission image T and an infrared reflection image F. The signal recognizing module 30 is configured to recognize whether the to-be-recognized bill has a fold. The receiving/rejecting module is configured to perform a receiving or rejecting operation on a to-be-recognized bill.

In particular, the signal recognizing module 30 further includes: a first high-pass filtering unit, a first low-pass filtering unit, a second high-pass filtering unit, a second low-pass filtering unit, a differential filtering image unit, a first characteristic extraction unit, a second characteristic extraction unit, a third characteristic extraction unit, a recognition decision unit. The first high-pass filtering unit is configured to filter the infrared transmission image T to obtain a high-pass infrared transmission filtering image gT. The first low-pass filtering unit is configured to filter the infrared transmission image T to obtain a low-pass infrared transmission filtering image dT. The second high-pass filtering unit is configured to perform high-pass filtering on the infrared reflection image F synchronously to the low-pass filtering performed on the infrared transmission image T according to a geometric coordinate point to point mapping relationship, to obtain a high-pass infrared reflection filtering image gF. The second low-pass filtering unit is configured to perform low-pass filtering on the infrared reflection image F synchronously to the high-pass filtering performed on the infrared transmission image T according to the geometric coordinate point to point mapping relationship, to obtain a low-pass infrared reflection filtering image dF. The differential filtering image unit is configured to perform a differential operation on the high-pass infrared reflection filtering image gF and the low-pass infrared transmission filtering image dT to obtain a differential filtering image cFT. The first characteristic extraction unit is configured to perform characteristic extraction on the high-pass infrared transmission filtering image gT by calculating an average gray value gT_G of the gT as a characteristic value. The second characteristic extraction unit is configured to perform characteristic extraction on the low-pass infrared reflection filtering image dF by calculating an average gray value dF_G of the dF as a characteristic value. The third characteristic extraction unit is configured to perform characteristic extraction on the differential filtering image cFT by calculating an average gray value cFT_G of the cFT as a characteristic value. The recognition decision unit is configured to calculate models for distinguishing folded bills and non-folded bills based on the characteristic value gT_G, the characteristic value dF_G and the characteristic value cFT_G of the sample bills and make a decision whether the to-be-recognized bill has a fold based on a bill classifying decision model. The bill classifying decision model is: in a case that $p_1 > T_1$, $p_2 > T_2$, $p_3 > T_3$ are all true, the to-be-recognized bill is recognized as a folded bill; in a case that $p_1 > T_1$, $p_2 > T_2$, $p_3 > T_3$ are not all true, the to-be-recognized bill is recognized as a non-folded bill, where $p_1$, $p_2$ and $p_3$ are confidence levels for determining the to-be-recognized bill as a folded bill, and $T_1$, $T_2$ and $T_3$ are three confidence level thresholds.

The bill classifying decision model may be further amended as:

$$p_s = \alpha * p_1 + \beta * p_2 + \gamma * p_3, \begin{cases} > T_s & \text{folded bill} \\ \leq T_s & \text{non-folded bill} \end{cases};$$

where, $p_1$, $p_2$ and $p_3$ are the confidence levels for determining the to-be-recognized bill as a folded bill, $\alpha, \beta, \gamma$ are different weighted values assigned to p1, p2 and p3 respectively, and $\alpha + \beta + \gamma = 1$, $\alpha \geq 0$, $\beta \geq 0$, $\gamma \geq 0$, $T_s$ is a threshold and has an empirical value of 0.5.

Hereinafter, a folded bill recognizing method executed by the folded bill recognizing device is described in detail.

Figure 2:
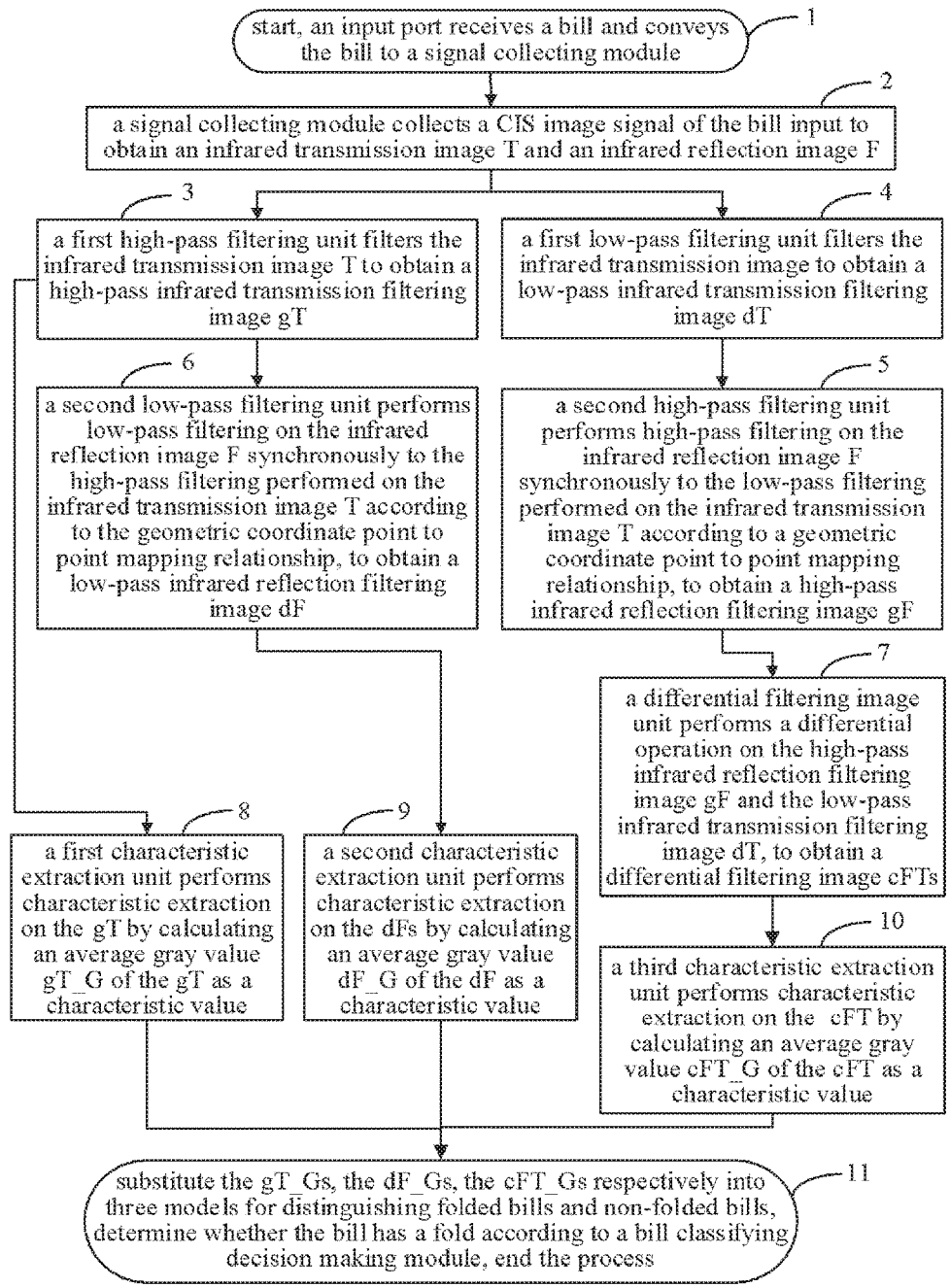
FIG. 2 is a flow chart of a folded bill recognizing method according to a preferred embodiment of the disclosure.

As shown in FIG. 2, the folded bill recognizing method includes the following step 1 to step 11. In step 1, a bill input port receives a to-be-recognized bill, and conveys the to-be-recognized bill to a signal collecting module. In step 2, a signal collecting module collects a CIS image signal of the to-be-recognized bill to obtain an infrared transmission image $T_s$ and an infrared reflection image $F_s$. In step 3, a first high-pass filtering unit filters the infrared transmission image $T_s$ to obtain a high-pass infrared transmission filtering image $gT_s$. In step 4, a first low-pass filtering unit filters the infrared transmission image to obtain a low-pass infrared transmission filtering image $dT_s$. In step 5, a second high-pass filtering unit performs high-pass filtering on the infrared reflection image $F_s$ synchronously to the low-pass filtering performed on the infrared transmission image $T_s$ according to a geometric coordinate point to point mapping relationship, to obtain a high-pass infrared reflection filtering image $gF_s$. In step 6, a second low-pass filtering unit performs low-pass filtering on the infrared reflection image $F_s$ synchronously to the low-pass filtering performed on the infrared transmission image $T_s$ according to a geometric coordinate point to point mapping relationship, to obtain a low-pass infrared reflection filtering image $dF_s$. In step 7, a differential filtering image unit performs a differential operation on the high-pass infrared reflection filtering image $gF_s$ and the low-pass infrared transmission filtering image $dT_s$ to obtain a differential filtering image $cFT_s$. In step 8, a first characteristic extraction unit performs characteristic extraction on the high-pass infrared transmission filtering image $gT_s$ by calculating an average gray value $gT\_G_s$ of the $gT_s$ as a characteristic value. In step 9, a second characteristic extraction unit performs characteristic extraction on the low-pass infrared reflection filtering image $dF_s$ by calculating an average gray value $dF\_G_s$ of the $dF_s$ as a characteristic value. In step 10, a third characteristic extraction unit performs characteristic extraction on the differential filtering image $cFT_s$ by calculating an average gray value $cFT\_G_s$ of the $cFT_s$ as a characteristic value. In step 11, the characteristic value $gT\_G_s$, the characteristic value $dF\_G_s$ and the characteristic value $cFT\_G_s$ are substituted respectively into three models $y_1, y_2, y_3$ for distinguishing folded bills and non-folded bills, $y_1 = f_1(gT\_G);$ $y_2 = f_2(dF\_G);$ $y_3 = f_3(cFT\_G);$ to obtain $p_1 = f_1(gT\_G_s);$ $p_2 = f_2(dF\_G_s);$ $p_3 = f_3(cFT\_G_s);$ where $p_1$, $p_2$ and $p_3$ are confidence levels for determining the to-be-recognized bill as a folded bill. Then whether the bill has a fold is determined according to the bill classifying decision module. The bill classifying decision module is: in a case that $p_1 > T_1$, $p_2 > T_2$, $p_3 > T_3$ are all true, the to-be-recognized bill is recognized as the folded bill; in a case that $p_1 > T_1$, $p_2 > T_2$, $p_3 > T_3$ are not all true, the to-be-recognized bill is recognized as a non-folded bill, where $T_1$, $T_2$ and $T_3$ are three confidence level thresholds. That is the end of the process.

Preferably, the step 11 further includes: assigning different weighted values $\alpha, \beta, \gamma$ to $p_1$, $p_2$ and $p_3$, where $\alpha + \beta + \gamma = 1$, $\alpha \geq 0$, $\beta \geq 0$, $\gamma \geq 0$. Then a threshold $T_s$ is determined. A bill classifying decision model is as follows:

$$p_s = \alpha * p_1 + \beta * p_2 + \gamma * p_3, \begin{cases} > T_s & \text{folded bill} \\ \leq T_s & \text{non-folded bill} \end{cases}.$$

Step 1 to step 10 are not executed in the listed sequence. Step 3 and step 4 may be executed at the same time. Step 5 and step 6 may be executed at the same time. Step 8 may be executed right after step 3. Step 9 may be executed right after step 6. Step 10 may be executed right after step 7.

Besides, the method for obtaining the three models $y_1, y_2, y_3$ for distinguishing folded bills and non-folded bills includes: collecting a certain number of samples of folded bills and non-folded bills; obtaining, for each of the samples, a characteristic value of an average gray value $gT\_G$ of a high-pass infrared transmission filtering image $gT$, a characteristic value of an average gray value $dF\_G$ of a low-pass infrared reflection filtering image $dF$ and a characteristic value of an average gray value $cFT\_G$ of a differential filtering image $cFT$; counting the characteristic value of the $gT\_G$, the characteristic value of the $dF\_G$ and the characteristic value of the $cFT\_G$ respectively, to obtain a probability distribution graph of the $gT\_G$, a probability distribution graph of the $dF\_G$ and a probability distribution graph of the $cFT\_G$ corresponding to the folded bills as the following formulas:

$y_1 = f_1(gT\_G);$ $y_2 = f_2(dF\_G);$ $y_3 = f_3(cFT\_G);$ where $y_1, y_2, y_3$ are the three models for distinguishing folded bills and non-folded bills respectively.

Particularly, the method for obtaining the characteristic value of the average gray value $gT\_G$ of the high-pass infrared transmission filtering image $gT$, the characteristic value of the average gray value $dF\_G$ of the low-pass infrared reflection filtering image $dF$ and the characteristic value of the average gray value $cFT\_G$ of the differential filtering image $cFT$ of each of the samples is the same as the method for obtaining the characteristic value of the average gray value $gT\_G_s$ of the high-pass infrared transmission filtering image $gT_s$, the characteristic value of the average gray value $dF\_G_s$ of the low-pass infrared reflection filtering image $dF_s$ and the characteristic value of the average gray value $cFT\_G_s$ of the differential filtering image $cFT_s$ of the to-be-recognized bill, i.e., step 1-step 10.

The folded bill recognizing method is illustrated with an example of a bill A.

Corresponding to step 1, the folded bill A is inputted to a receiving port of a self-service device.

Corresponding to step 2, when the bill A passes through the signal collecting module 20 by means of mechanical conveying, the signal collecting module 20 collects signals of the bill A. A collected CSI infrared transmission image signal is $rT$, and an infrared reflection image signal is $rF$.

Before step 3, a high-pass filter threshold and a low-pass filter threshold for the image signal $rT$ and $rF$ are calculated firstly. An average gray value of the $rT$ is calculated first as:

$$avG = \sum_{i=1}^{w*h} pix(i)/(w*h) \tag{9}$$

where $pix(i)$ is a gray value corresponding to a pixel of $rT$, $w$ is the width of the image signal $rT$, $h$ is the height of the image signal $rT$.

The high-pass filter threshold corresponding to $rT$ is $T_{11} = j*avG, 1 \leq j \leq (255/avG)$, the low-pass filter threshold corresponding to $rT$ is $T_{22} = k*avG, 0 \leq k \leq 1$.

Corresponding to step 3, high-pass filtering is performed on $rT$ by the first high-pass filtering unit to obtain a high-pass filtering image GT.

Corresponding to step 4, low-pass filtering is performed on $rT$ by the first low-pass filtering unit to obtain a low-pass filtering image DT.

Corresponding to step 5, corresponding high-pass filtering is performed on $rF$ according to a geometric coordinate mapping relationship, to obtain a high-pass filtering image GF.

Corresponding to step 6, corresponding low-pass filtered is performed on $rF$ according to a geometric coordinate mapping relationship, to obtain a low-pass filtering image DF.

Corresponding to step 7, differential operation is performed on the high-pass filtering image GF and the loss-pass filtering image DT, to obtain a differential filtering image CFT.

Corresponding to step 10, an average gray value cAVG of the differential filtering image CFT is calculated as a characteristic value, with the same calculating model as formula (9).

Corresponding to step 9, an average gray value dAVG of the loss-pass filtering image DF is calculated as a characteristic value, with the same calculating model as formula (9).

Corresponding to step 8, an average gray value gAVG of the high-pass filtering image GT is calculated as a characteristic value, with the same calculating model as formula (9).

Corresponding to step 11, the calculated cAVG, dAVG and gAVG are input to a multi-characteristic fusion decision unit, and classification is performed by learnt multi-characteristic classifying probability distribution models $f_1(x_1)$, $f_2(x_2)$, $f_3(x_3)$. If $f_1(cABG)>T_1$, $f_2(dAVG)>T_2$, $f_3(gAVG)>T_3$, where $T_1$, $T_2$ and $T_3$ are empirical thresholds which generally are 0.5, that is, if an output of the decision making unit is true, the bill A is recognized as a folded bill, and if an output of the decision making unit is false, the bill A is recognized as a non-folded bill. The process of recognizing ends.

In the folded bill recognizing method and folded bill recognizing device provided by the embodiment, a method of high/low pass filters are adopted to effectively classify characteristics, a distinguishability of the characteristics is highly improved. Particularly, different characteristics correspond to different classifiers. Among the classifiers, they have functions similar to the Adaboost classifier, which may ensure a recognition confidence level of the recognizing device of the disclosure and make the recognition system more robustly compatible with complex situations such as an environmental interference, a fouled bill. The folded bill recognizing method and device can effectively recognize a folded bill.

The above is only description of the preferred embodiments of the disclosure. It should be noted that, the above preferred embodiments should not be considered as the limits to the disclosure. The protective scope of the disclosure should be based on the scope limited by the claims. For those skilled in the art, modifications and retouching can be made without departing from the spirit or scope of the disclosure. The modifications and retouching are also in the protective scope of the disclosure.

The invention claimed is:

1. A method for recognizing a folded bill, performed by a folded bill recognizing device, comprising:
    obtaining
    an infrared transmission image $T_s$ and an infrared reflection image $F_s$ of a to-be-recognized bill;
    performing high-pass filtering on the infrared transmission image $T_s$ to obtain a high-pass infrared transmission filtering image $gT_s$;
    performing low-pass filtering on the infrared transmission image $T_s$ to obtain a low-pass infrared transmission filtering image $dT_s$;
    performing high-pass filtering on the infrared reflection image $F_s$, to obtain a high-pass infrared reflection filtering image $gF_s$, wherein the high-pass filtering on the infrared reflection image $F_s$ and the low-pass filtering on the infrared transmission image $T_s$ are performed synchronously according to a geometric coordinate mapping relationship;
    performing low-pass filtering on the infrared reflection image $F_s$, to obtain a low-pass infrared reflection filtering image $dF_s$, wherein the low-pass filtering on the infrared reflection image $F_s$ and the high-pass filtering on the infrared transmission image $T_s$ are performed synchronously according to the geometric coordinate mapping relationship;
    performing a differential operation on the high-pass infrared reflection filtering image $gF_s$ and the low-pass infrared transmission filtering image $dT_s$ to obtain a differential image $cFT_s$;
    performing a first characteristic extraction on the high-pass infrared transmission filtering image $gT_s$ by calculating an average gray value $gT\_G_s$ of the $gT_s$ as a characteristic value;
    performing a second characteristic extraction on the low-pass infrared reflection filtering image $dF_s$ by calculating an average gray value $dF\_G_s$ of the $dF_s$ as a characteristic value;
    performing a third characteristic extraction on the differential image $cFT_s$ by calculating an average gray value $cFT\_G_s$ of the $cFT_s$ as a characteristic value;
    substituting the characteristic value $gT\_G_s$, the characteristic value $dF\_G_s$ and the characteristic value $cFT\_G_s$ respectively into three models $y_1, y_2, y_3$ for distinguishing folded bills and non-folded bills, $$y_1 = f_1(gT\_G);$$

$$y_2 = f_2(dF\_G)$$

$$y_3 = f_3(cFT\_G)$$

to obtain $$p_1 = f_1(gT\_G_s);$$

$$p_2 = f_2(dF\_G_s)$$

$$p_3 = f_3(cFT\_G_s);$$

wherein $p_1$, $p_2$ and $p_3$ are confidence levels for determining the to-be-recognized bill as a folded bill; f1, f2 and f3 indicate learnt multi-characteristic classifying probability distribution models; in a case that $p_1>T_1$, $p_2>T_2$, $p_3>T_3$ are all true, the to-be-recognized bill is recognized as a folded bill; in a case that $p_1>T_1$, $p_2>T_2$, $p_3>T_3$ are not all true, the to-be-recognized bill is recognized as a non-folded bill, where $T_1$, $T_2$ and $T_3$ are three confidence level thresholds.

2. The method according to claim 1, wherein the substituting further comprises:
    assigning different weighted values $\alpha, \beta, \gamma$ to $p_1$, $p_2$ and $p_3$, wherein $\alpha+\beta+\gamma=1, \alpha\geq0, \beta\geq0, \gamma\geq0$; and
    determining a threshold $T_s$, wherein
    the bill classifying decision model is:

$$p_s = \alpha * p_1 + \beta * p_2 + \gamma * p_3, \begin{cases} > T_s & \text{folded bill} \\ \leq T_s & \text{non-folded bill} \end{cases}.$$

3. The method according to claim 1, further comprising obtaining the three models $y_1, y_2, y_3$ for distinguishing folded bills and non-folded bills, the obtaining comprising:
    collecting a certain number of samples of folded bills and non-folded bills;
    obtaining, for each of the samples, a characteristic value of an average gray value $gT\_G$ of a high-pass infrared transmission filtering image gT, a characteristic value of an average gray value $dF\_G$ of a low-pass infrared reflection filtering image dF and a characteristic value of an average gray value $cFT\_G$ of a differential filtering image cFT;
    counting the characteristic value of the $gT\_G$, the characteristic value of the $dF\_G$ and the characteristic value of the $cFT\_G$ respectively, to obtain a probability distribution graph of the $gT\_G$, a probability distribution graph of the dF_G and a probability distribution graph of the cFT_G corresponding to the folded bills as the following formulas:

$$y_1 = f_1(gT\_G);$$
$$y_2 = f_2(dF\_G)$$
$$y_3 = f_3(cFT\_G);$$

wherein $y_1, y_2, y_3$ are the three models for distinguishing folded bills and non-folded bills respectively.

4. The method according to claim 3, wherein a method for obtaining, for each of the samples, the characteristic value of the average gray value gT_G of the high-pass infrared transmission filtering image gT, the characteristic value of the average gray value dF_G of the low-pass infrared reflection filtering image dF and the characteristic value of the average gray value cFT_G of the differential filtering image cFT is the same as the method for obtaining the characteristic value of the average gray value $gT\_G_s$ of the high-pass infrared transmission filtering image $gT_s$, the characteristic value of the average gray value $dF\_G_s$ of the low-pass infrared reflection filtering image $dF_s$ and the characteristic value of the average gray value $cFT\_G_s$ of the differential filtering image $cFT_s$ of the to-be-recognized bill.

5. The method according to claim 3, wherein a method for obtaining the three models $y_1, y_2, y_3$ for distinguishing folded bills and non-folded bills comprises:
   collecting a certain number of samples of folded bills and non-folded bills;
   obtaining, for each of the samples, a characteristic value of an average gray value gT_G of a high-pass infrared transmission filtering image gT, a characteristic value of an average gray value dF_G of a low-pass infrared reflection filtering image dF and a characteristic value of an average gray value cFT_G of a differential filtering image cFT;
   counting the characteristic value of the gT_G, the characteristic value of the dF_G and the characteristic value of the cFT_G respectively, to obtain a probability distribution graph of the gT_G, a probability distribution graph of the dF_G and a probability distribution graph of the cFT_G corresponding to the folded bills as the following formulas:

$$y_1 = f_1(gT\_G);$$
$$y_2 = f_2(dF\_G);$$
$$y_3 = f_3(cFT\_G);$$

wherein $y_1, y_2, y_3$ are the three models for distinguishing folded bills and non-folded bills respectively.

6. The method according to claim 5, wherein a method for obtaining, for each of the samples, the characteristic value of the average gray value gT_G of the high-pass infrared transmission filtering image gT, the characteristic value of the average gray value dF_G of the low-pass infrared reflection filtering image dF and the characteristic value of the average gray value cFT_G of the differential filtering image cFT is the same as the method for obtaining the characteristic value of the average gray value $gT\_G_s$ of the high-pass infrared transmission filtering image $gT_s$, the characteristic value of the average gray value $dF\_G_s$ of the low-pass infrared reflection filtering image $dF_s$ and the characteristic value of the average gray value $cFT\_G_s$ of the differential filtering image $cFT_s$ of the to-be-recognized bill.

7. The method according to claim 1, wherein the method further comprises:
prior to performing the high-pass filtering on the infrared transmission image $T_s$,
calculating a high-pass filter threshold and a low-pass filter threshold for the image signals $T_s$ and $F_s$ by:
calculating an average gray value of the $T_s$ as:

$$avG = \sum_{i=1}^{w*h} pix(i)/(w*h);$$

where pix(i) is a gray value corresponding to a pixel of $T_s$, w is the width of the image signal $T_s$, h is the height of the image signal $T_s$; and
calculating the high-pass filter threshold corresponding to $T_s$ as $T_{11} = j*avG, 1 \leq j \leq (255/avG)$, and the low-pass filter threshold corresponding to $T_s$ as $T_{22} = k*avG$, $0 \leq k \leq 1$.

8. The method according to claim 7, wherein a calculating model for calculating the average gray value $gT\_G_s$ of the $gT_s$, a calculating model for calculating the average gray value $dF\_G_s$ of the $dF_s$ and a calculating model for calculating the average gray value $cFT\_G_s$ of the $cFT_s$ are the same as the calculating models for calculating the average gray values of the $T_s$.

9. A method for recognizing a folded bill, comprising:
obtaining an infrared transmission image $T_s$ and an infrared reflection image $F_s$ of a to-be-recognized bill;
performing high-pass filtering on the infrared transmission image $T_s$ to obtain a high-pass infrared transmission filtering image $gT_s$;
performing low-pass filtering on the infrared transmission image $T_s$ to obtain a low-pass infrared transmission filtering image $dT_s$;
performing a first characteristic extraction on the high-pass infrared transmission filtering image $gT_s$ by calculating an average gray value $gT\_G_s$ of the $gT_s$ as a characteristic value;
performing high-pass filtering on the infrared reflection image $F_s$, to obtain a high-pass infrared reflection filtering image $gF_s$, wherein the high-pass filtering on the infrared reflection image $F_s$ and the low-pass filtering on the infrared transmission image $T_s$ are performed synchronously according to a geometric coordinate mapping relationship;
performing low-pass filtering on the infrared reflection image $F_s$ to obtain a low-pass infrared reflection filtering image $dF_s$, wherein the low-pass filtering on the infrared reflection image $F_s$ and the high-pass filtering on the infrared transmission image $T_s$ are performed synchronously according to the geometric coordinate mapping relationship;
performing a second characteristic extraction on the low-pass infrared reflection filtering image $dF_s$ by calculating an average gray value $dF\_G_s$ of the $dF_s$ as a characteristic value;
performing a differential operation on the high-pass infrared reflection filtering image $gF_s$ and the low-pass infrared transmission filtering image $dT_s$ to obtain a differential image $cFT_s$;
performing a third characteristic extraction on the differential image $cFT_s$ by calculating an average gray value $cFT\_G_s$ of the $cFT_s$ as a characteristic value; and
substituting the characteristic value $gT\_G_s$, the characteristic value $dF\_G_s$ and the characteristic value $cFT\_G_s$ respectively into three models $y_1, y_2, y_3$ for distinguishing rippled bills and non-rippled bills, $y_1 = f_1(gT\_G)$;

$y_2 = f_2(dF\_G)$ $y_3 = f_3(cFT\_G)$;

to obtain $p_1 = f_1(gT\_G_s)$;

$p_2 = f_2(dF\_G_s)$ $p_3 = f_3(cFT\_G_s)$;

wherein $p_1$, $p_2$ and $p_3$ are confidence levels for determining the to-be-recognized bill as a rippled bill; f1, f2 and f3 indicate learnt multi-characteristic classifying probability distribution models; in a case that $p_1 > T_1$, $p_2 > T_2$, $p_3 > T_3$ are all true, the to-be-recognized bill is recognized as a rippled bill; in a case that $p_1 > T_1$, $p_2 > T_2$, $p_3 > T_3$ are not all true, the to-be-recognized bill is recognized as a non-rippled bill, where $T_1$, $T_2$ and $T_3$ are three confidence level thresholds.

* * * * *

UNITED STATES PATENT AND TRADEMARK OFFICE
CERTIFICATE OF CORRECTION

PATENT NO. : 10,319,170 B2
APPLICATION NO. : 15/544379
DATED : June 11, 2019
INVENTOR(S) : Guanglu Liu et al.

Page 1 of 1

It is certified that error appears in the above-identified patent and that said Letters Patent is hereby corrected as shown below:

In the Claims

At Column 11, Claim 5, Line 25, please delete "a method for".

At Column 12, Claim 7, Line 1, please replace -- filtering-on -- with "filtering on".

Signed and Sealed this
Tenth Day of September, 2019

Andrei Iancu
*Director of the United States Patent and Trademark Office*